United States Patent [19]
Weisse

[11] Patent Number: 5,910,838
[45] Date of Patent: Jun. 8, 1999

[54] METHOD OF DETERMINING CONCENTRATIONS BY MEANS OF CONTINUOUS-SPECTRUM ATOMIC ABSORPTION SPECTROSCOPY

[75] Inventor: Renate Weisse, Berlin, Germany

[73] Assignee: Bodenseewerk Perkin-Elmer GmbH, Uberlingen, Germany

[21] Appl. No.: 08/840,953

[22] Filed: Apr. 21, 1997

[30] Foreign Application Priority Data

Apr. 19, 1996 [DE] Germany .............................. 196 17 100

[51] Int. Cl.⁶ ...................................................... G01J 3/30
[52] U.S. Cl. ............................................ 356/312; 356/307

[58] Field of Search ....................................... 356/312, 307, 356/311, 315

[56] References Cited

U.S. PATENT DOCUMENTS

4,300,833  11/1981  Harnly et al. ............................ 356/312

Primary Examiner—K. P. Hantis
Attorney, Agent, or Firm—David Aker

[57] ABSTRACT

In a method of determining concentrations by means of atomic absorption spectrometry, the absorption of structured background is determined in a graphite furnace.

9 Claims, 6 Drawing Sheets

METHOD OF DETERMINING CONCENTRATIONS BY MEANS OF CONTINUOUS-SPECTRUM ATOMIC ABSORPTION SPECTROSCOPY

TECHNICAL FIELD

The present invention relates to a method of determining concentrations by means of continuous-spectrum atomic absorption spectroscopy.

BACKGROUND ART

A measuring light beam which is emitted from a line-emitting light source is produced in standard atomic absorption spectroscopy. The light source, for instance a hollow-cathode lamp, emits a line spectrum which corresponds to the resonance lines of a specific element to be determined. The measuring light beam is passed through an atomizing region in which the atoms of a sample are present in their atomic state. Such an atomizing region may, for instance, be the interior of a graphite furnace in which the sample is electrothermally atomized. In the atomizing region the measuring light beam is subjected, due to the atomic vapor, to a time-dependent specific absorption which depends on the amount of the element to be determined in the sample. The measuring light beam will then pass through a medium resolution monochromator which only allows the passage of a specific line from the line spectrum. The measuring light beam will then fall onto a single detector, normally a photomultiplier. It is only a single element which can respectively be determined in this way at one time, namely the element whose resonance lines are emitted from the light source.

Furthermore, it is known that a reference light beam is passed through the atomizing region onto a detector alternately with the measuring light beam emitted from the hollow-cathode lamp in order to compensate for the effect of background absorption. Such a reference light beam has a bandwith which is large in comparison with the line width of the hollow-cathode lamp. As a result, the reference light beam remains virtually unaffected by the specific absorption by the sample atoms.

Another way of compensating for background absorption consists of applying a strong magnetic field to the light source or the atomized sample in a periodic manner. The emitted spectral lines and the absorption lines are thereby split up due to the Zeeman effect. There is a periodic relative shift between the spectral lines absorbed by the sample atoms and the spectral lines emitted by the light source. Background absorption is normally not influenced by a magnetic field, whilst the specific atomic absorption is absent upon application of a magnetic field. The pure atomic absorption which is corrected with respect to background absorption can be determined by subtraction.

Furthermore, there are known atomic absorption spectrometers which make use of a continuous source of radiation in combination with a high-resolution spectrometer and a multitude of detector elements. In these atomic absorption spectrometers the background absorption is determined by measuring the absorption in the direct vicinity of the analysis line. The specific absorption is then determined by subtracting the background absorption determined in this way from the total absorption which was measured on the analysis wavelength. The respective spectral region in which the background is determined is selected in that the spectrum is evaluated by the person who performs the measurement.

DISCLOSURE OF THE INVENTION

In cases where a sample contains not only atoms of the element to be determined, but also molecules and other atoms effecting an absorption within the spectral bandwidth of the monochromator, the magnitude of this absorption must be determined and corrected. If such a background shows a non-linear dependance on the wavelength, this points to a structured background. Hence, problems may arise particularly from the correction of structured backgrounds by means of a continuous radiation source as a reference light beam in line AAS in which spectrometers of a medium resolution are used. In most cases such interferences can be corrected by employing the Zeeman method. However, examples are also known in which an incorrect background correction is made with this type of method. This is particularly the case when the analysis line has arranged directly next thereto the atom line of another element which is also split up by the magnetic field and then passes into the spectral region of the emission line of the line source.

As a result, background absorption is overrated and an overcompensation in the calculation of the analysis concentration is effected. In another group the background stems from structured molecule spectra which exhibit a Zeeman effect. In this case an overcompensation or undercompensation may be observed. The molecule spectra normally consist of a great number of closely adjacent rotation lines, which are the vibrational bands of an electronic transition of a molecule. In continous-spectrum atomic absorption spectrometry a method has so far been used which can correct both broad-band and structured backgrounds. The correction of a structured background, however, has only been possible in cases where the background could be fully separated in time or spectrally from the specific absorption. Even in the case of high resolution, this is not always possible because the absorption line widths are subject to pressure and Doppler broadening. A separation in time is only observed in exceptional cases and greatly depends on the matrix of the sample, the temperature program used for the graphite furnace atomizer and the atomizing characteristics of the elements. Interference can be reduced by employing a suitable temperature program and suitable modifiers, whereby the signal-to-noise ratio of the absorption signal is improved. This, however, presupposes that the reaction mechanisms inside the graphite furnace are known.

It is the object of the present invention to improve the accuracy of concentration determinations by means of atomic absorption spectrometry.

Another object of the present invention is to determine the absorption of structured background in a graphite furnace.

According to the present invention this object is achieved in that for the determination of concentrations by means of atomic absorption spectrometry
  a) a continuous source is used as a radiation source;
  b) a high-resolution spectrometer is used as a dispersive element;
  c) a detector is used which consists of a multitude of detector elements and
  d) steps are taken for determining the specific absorption, which steps are characterized in that
    (i) The radiation intensity of the source impinging on each detector element is determined.
    (ii) A sample containing a known element to be quantified and possibly some unknown components is introduced into the spectrometer and an uncorrected absorbance is determined at each detector element over a series of times to make up an uncorrected absorbance spectrum over time.
    (iii) A broadband background absorbance function is determined from the uncorrected absorbances by choosing correlation coefficients that correspond to the local minima of the uncorrected absorbance spectrum.

(iv) A broadband absorbance is calculated for each detector element and is subtracted from the uncorrected absorbance for each detector element yielding a first corrected absorbance.

(v) The first corrected absorbance at the particular detector corresponding to the known element line at each particular time is compared to absorbances measured by adjacent detectors at each particular time. Differences that fluctuate by more than a predetermined value over time indicate the presence of an additional line or lines caused by unknown components in the sample that are interfering with the absorbance of the known element.

(vi) The interfering line is then identified as due to an interfering atom or an interfering molecule. For an interfering atom, the profile is measured prior to sample measurement. For an interfering molecule the profile of the molecule line is determined on another isolated molecule line in the measured spectral region.

(vii) The spectral position of the peak maximum of the interfering line is determined at the particular time that the interfering absorption is maximum relative to the analysis absorption.

(viii) The magnitude of the absorbance of the interfering line where it is superimposed on the analysis line is calculated from the position and profile of the interference line and is subtracted from the absorbance of the analysis line.

The object of the present invention is most readily achieved when the spectral bandwidth of the spectrometer is, at most, a few multiples of the half width of the analysis line.

In a spectrum containing a wavelength-dependent broadband portion, a multi-lined molecule spectrum may also be superposed next to the analysis line. Hence, it does not suffice to resolve the individual peaks next to the analyis line, but the broad-band portion also must be determined. To this end, the local minima of the spectrum are determined and a function is fitted thereto. This function may, for instance, be a polynomial. When subtracting this polynomial from the spectrum, one obtains a spectrum of individual peaks in which the extinction on the detector elements, on which the minima were located, is just zero. However, an interfering line may still overlap with the analysis line so that further correction measures must be taken. First, it must be determined whether such an interference exists at all. To this end, the absorbance over time on the peak pixel (PP) and the adjacent pixels (PP+/-1), (PP+/-2), . . . (PP+/-x) is considered. In the absence of an interference, their relation A(PP+/-x)/A(PP) is constant in time. If this is not the case, there is an inference and it is possible to select with the maximum of the quotient the individual spectrum in which the interference is maximum and the information on the interference molecule can most easily be obtained.

The half width of the interfering line can be estimated in this individual spectrum on the basis of another line of the interference molecule. The exact wavelength of the maximum of the interfering line can be calculated on the assumption of, for example, a Gauss-like line profile. The height of the maximum of the interfering line from which follows the magnitude of the interference on the analysis line as well as its profile is then determined from the original spectrum integrated over time.

BRIEF DESCRIPTION OF THE DRAWINGS

An embodiment of the present invention will now be explained in more detail with reference to the associated drawings, in which.

DETAILED DESCRIPTION OF THE PREFERRED EMBODIMENT

Figure 1:
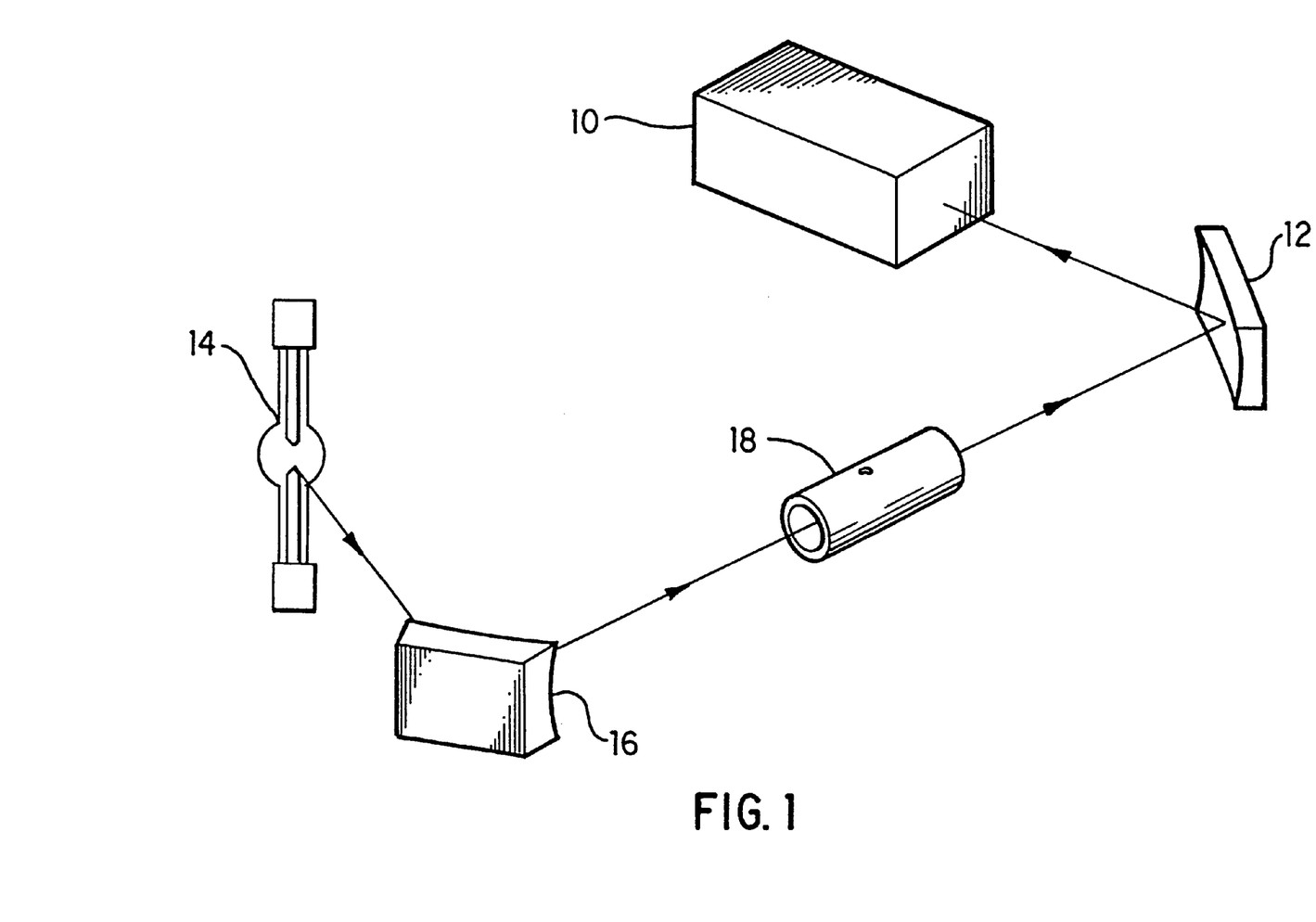
FIG. 1 shows the structure of a continuous-spectrum atomic absorption spectrometer.
Figure 2:
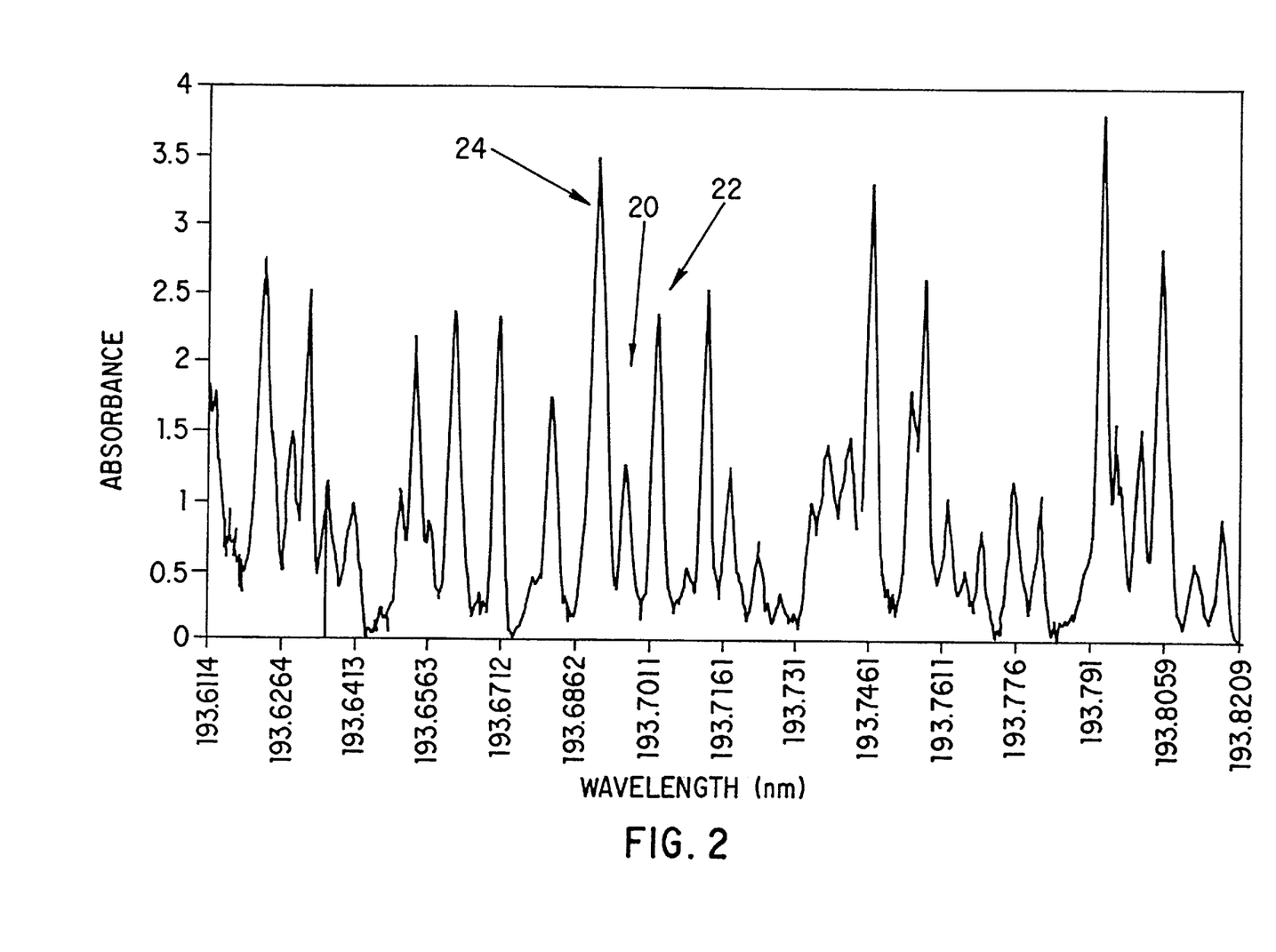
FIG. 2 shows an absorption spectrum obtained by atomizing arsenic with $NH_4H_2PO_4$.
Figure 3:
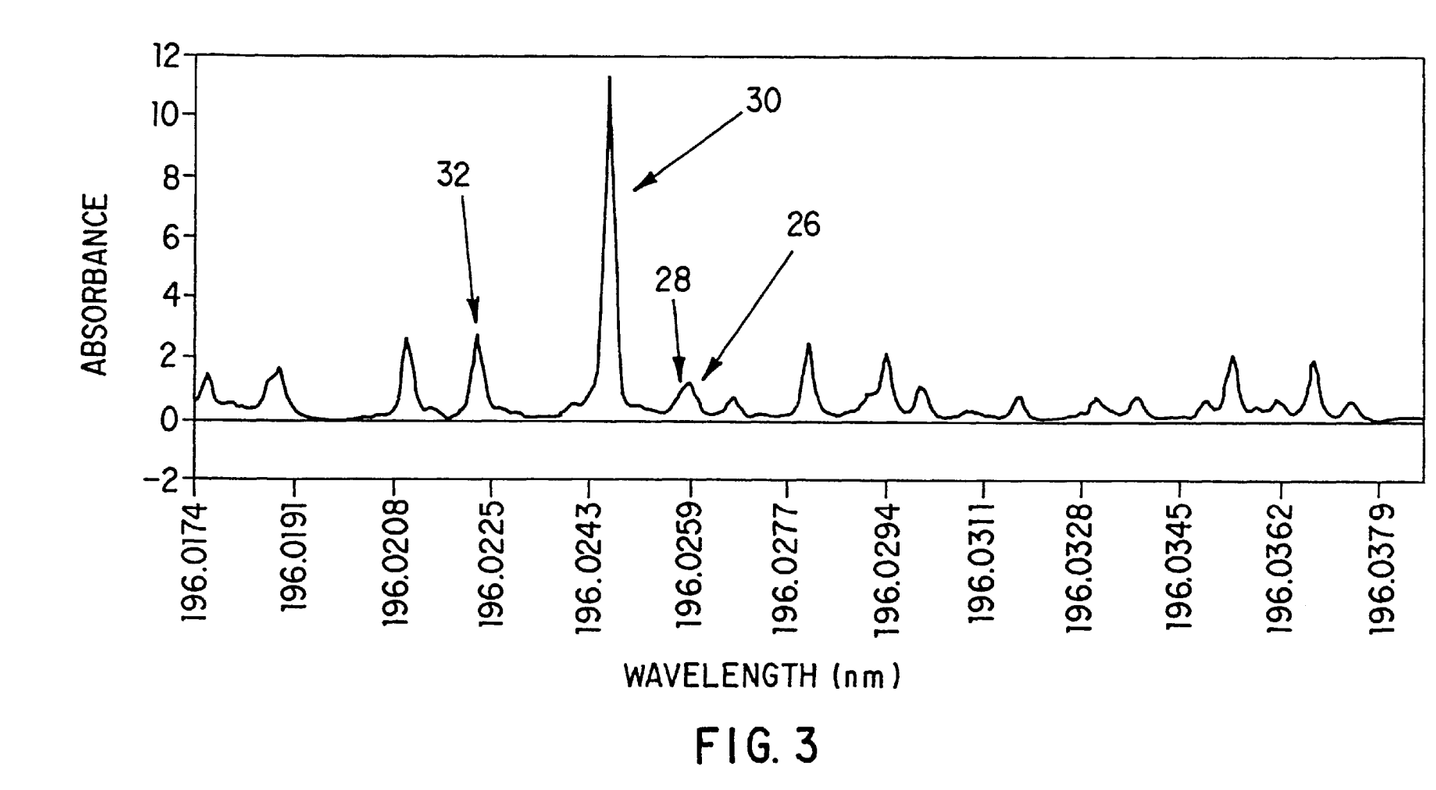
FIG. 3 shows an absorption spectrum obtained by atomizing selenium with $NH_4H_2PO_4$.

In FIG. 1, reference numeral 14 designates a xenon high-pressure short-arc lamp which emits a measuring light beam having a continuous spectrum. The measuring light beam is focused by a toric mirror 16 into the hole of a graphite furnace 18. The divergent measuring light beam exiting from the graphite furnace 18 is collected by a toric mirror 12. The measuring light beam, which is again convergent, will then fall onto the entrance slit of a high-resolution spectrometer 10 in the exit slit plane of which there is provided a CCD line which passes the intensity values on to a computer. The spectrometer 10 is a double-echelle monochromator having a resolution of 100,000. FIG. 2 illustrates an absorbance spectrum as is obtained when the radiation from the continuous-spectrum source is absorbed by arsenic at 193 nm and huge amounts of $NH_4H_2PO_4$ exist in the sample. A strongly structured molecule spectrum is found next to the arsenic peak 20. The arsenic peak 20 is exactly positioned between two molecule peaks 22 and 24. When selenium is atomized in the presence of $HN_4H_2PO_4$ and palladium, a different situation will arise, as can be seen in FIG. 3. The selenium peak 26 overlaps with a molecule peak 28 to such a great extent that even in the case of a high spectral resolution the separation of the peaks is inadequate. With a greatly extended absorbance axis, as is the case in FIG. 4, it can be seen that next to the molecule peak 36 there is also a broad-band, wavelength-dependent portion in the spectrum. To quantify this portion, a function 38 is determined which describes the local minima 34 of the spectrum. This function is obtained according to a pattern as is illustrated in Table 1:

TABLE 1

Figure 4:
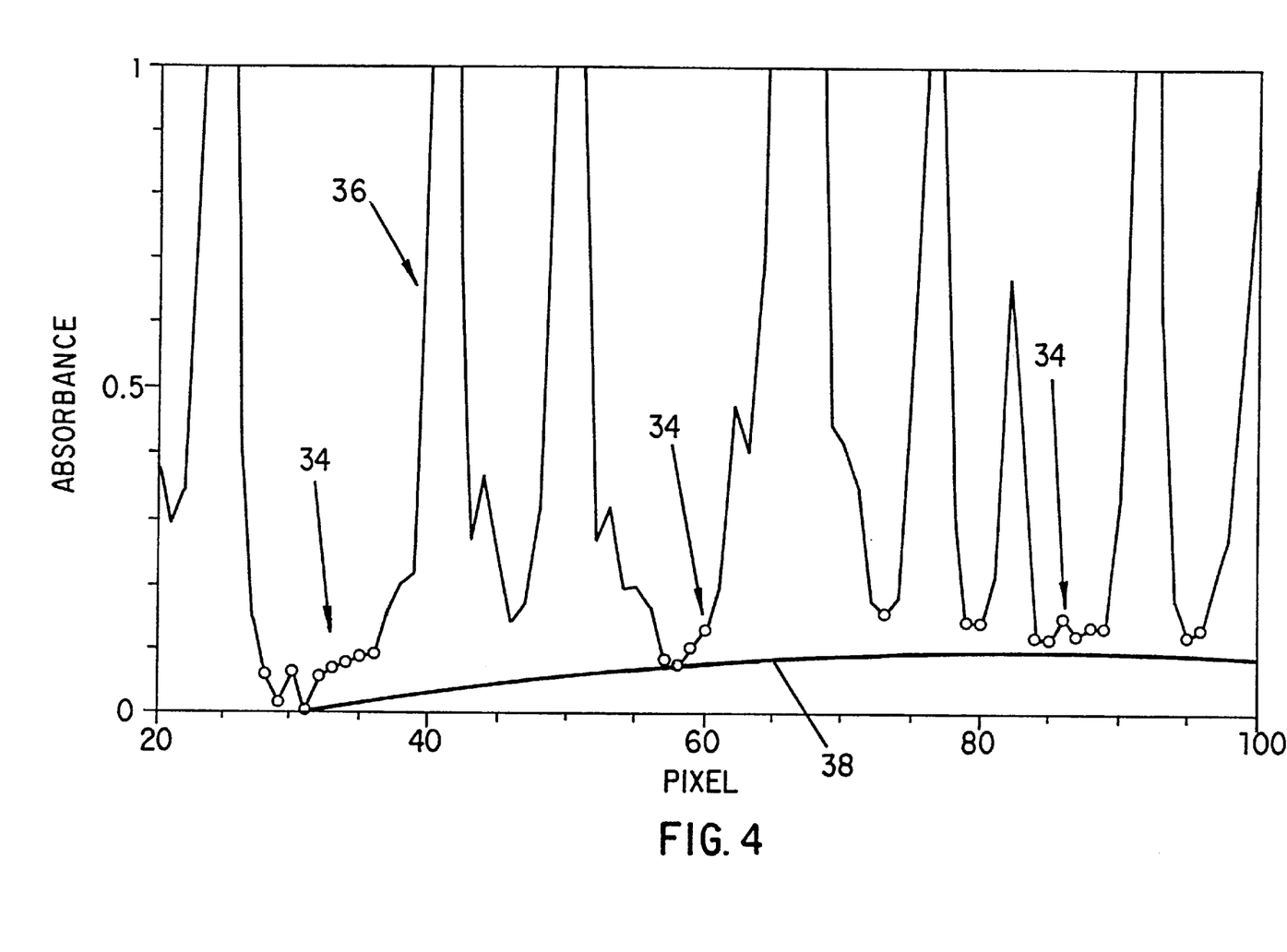
FIG. 4 shows an absorption spectrum which has marked therein the local minima with the aid of which the optimum function is determined for describing the wavelength-dependent broad-band background.

Illustration of the method for determining and correcting broad-band, wavelength-dependent background Select UGK pixel (= Untergrund-
korrektur [background correction])
calculate spectrum A(pixel)
window = 7 pixels
Inc (window)        calculate minimum in each window
[Inc = increment]
                lay 2nd order polynomial through minima
                remember optimum correlation coefficient
                window > pixel number/4
A(pix) = A(pix) polynomial with optimum correl. coeffic. (pix)
calculate standard deviation from A
T=15

TABLE 1-continued

Illustration of the method for determining and correcting broad-band, wavelength-dependent background

| Dec (T) [Dec = decriment] | IF A(pixel) < stand. dev./T THEN the pixel is a correction pixel T=1 OR 40 correction pixels found |
|---|---|

The local minima 34 by which function 38 (here a 2nd order polynomial) is defined are here designated as correction pixels, as are those that lie around the function values within an absorbance width of a standard deviation.

Figure 5:
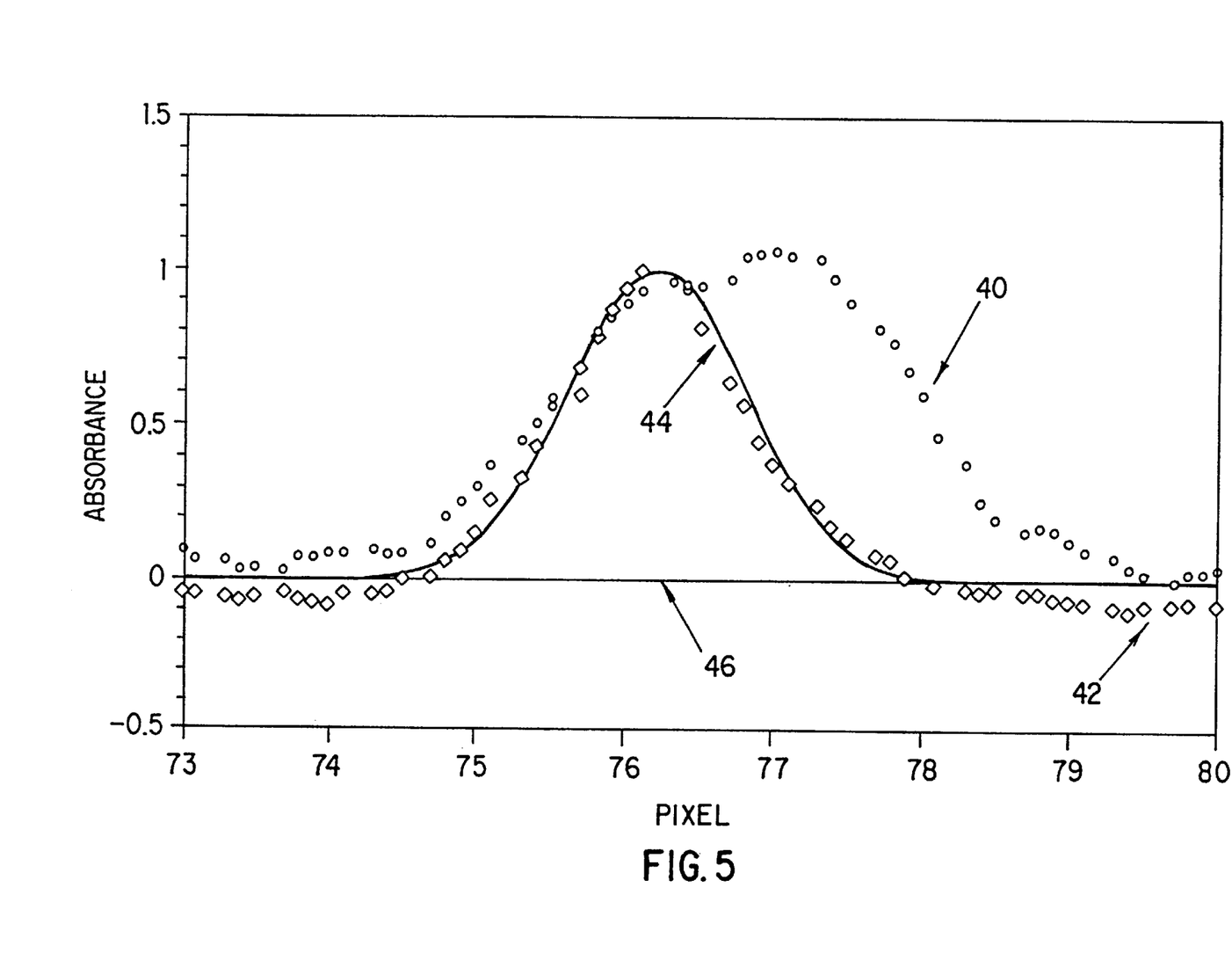
FIG. 5 shows a spectral section in which the spectral overlap of the analysis line with an interfering line is illustrated, as well as the calculated profile function of the interfering line.
Figure 6:
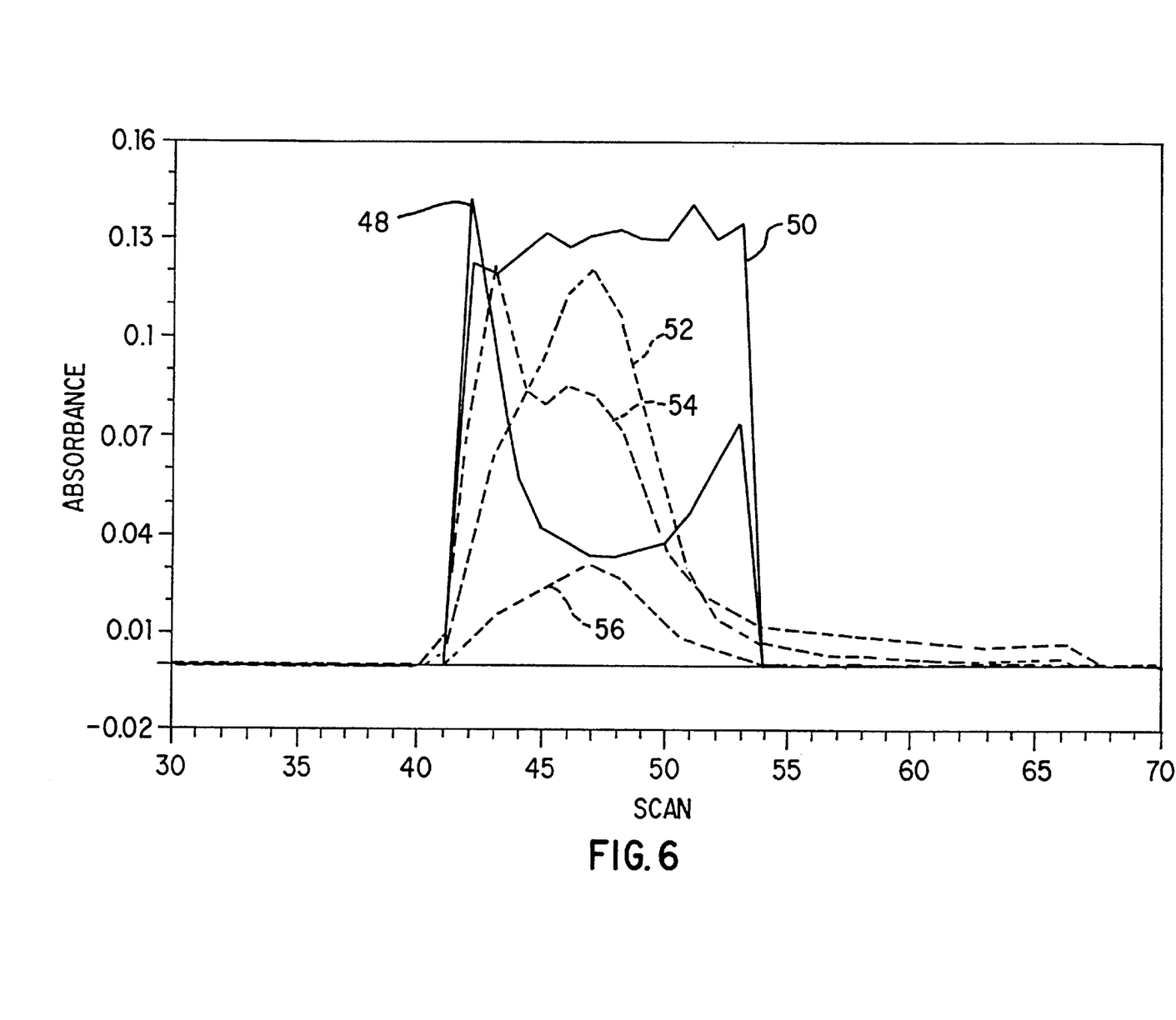
FIG. 6 shows the absorbance over time as measured by the peak pixel and the adjacent pixels and their quotients.

After correction of the broad-band, wavelength-dependent background, there may arise a situation as is illustrated in FIG. 5. The measurement curves designated by 40 and 42 follow from 10 absorption measurements in which the wavelength has been shifted by 1/10 pixel, so that a higher resolution could be achieved with 10 measurement points per pixel. Curve 40 describes the spectrum of a selenium line which is interfered with by a molecule line at a distance of less than 1 pixel (8 points). Curve 42 describes the same spectrum without selenium. To determine whether such an interference is present, the procedure is as shown in FIG. 6. At every point of time the quotients of the absorbance values 52 and 56 of the adjacent pixels on the wings of the analysis line are formed with the extinction values 54 on the peak pixel. This yields a time curve as is also shown in FIG. 6. In the absence of an interference, the quotients must be constant in time, as is illustrated in graph 50. By contrast, in the presence of an interference, the quotients have a time dependance as shown in graph 48. For an evaluation as to whether graph 50 is constant, it is possible to form the mean time value and standard deviation of the quotients and it can then be checked whether all values are within an interval of, for instance, two standard deviations around the mean value. With the quotients as are illustrated in graph 48, this is not the case. Hence, there is an interference. To avoid great values for quotients which are obtained when neither the peak pixel nor the adjacent pixels show values greater than a standard deviation, only quotients are formed in which the denominator is greater than a standard deviation.

It can be seen with reference to quotient 48 when the interference is maximum relative to the specific signal. In FIG. 6, this is the case with the 41st scan. Hence, most of the information on the spectrum of the interference molecule is obtained in the 41st measured spectrum. To determine the magnitude of interference on the analysis line, 3 parameters must be determined: the position of the peak maximum 46, the width of the peak and the height of the peak. With a suitable profile function (a Gauss function was chosen in FIG. 5), it is possible to determine the absorbance value of the interfering line on the peak wavelength of the analysis line. The width of the interference line can be determined on the basis of a different molecule line (designated by 32 in FIG. 3). Together with the Gauss function and the (non-interfered) absorbance values on the maximum of the interfering line and the pixel which lies at the other side of the interfering line (i.e. not on the analysis line side), one obtains the calculated maximum of the interfering line and its position. The magnitude of the interference is thus determined and can be subtracted from the absorbance value on the wavelength of the analysis peak. Table 2 once again illustrates the method of correcting overlapping lines.

A situation in which the interference is caused by an atom line is less problematic. In such a case the line profile and the exact position can easily be determined from a previous measurement in which a solution containing only the interfering element was introduced into the graphite furnace. This is normally not possible with molecules, since the molecules are very short-lived in part, and their occurrence depends on the matrix of the sample.

TABLE 2

Method of determining the background by overlapping lines

Procedure regarding automatic evaluation
select UGK pixel
calculate time peak
form quotient A(PP +/−1)/A(PP) for each scan
IF maximum (quotient) > mean value + 2*stand. deviat.
THEN interference exists
calculate individual spectrum for the scan with max (quotient)
determine peak pixel PP of the interfering line in the individual spectrum
Are there further lines of the interference molecule?

| NO | YES |
|---|---|
| Assume | search for further line of the interference molecule |
| half width | => peak pixel = PP2 and calc. maximum = max2 select UGK pixel |
| select | a= ln(A[pp2−1]/A[pp2] /ln(A[pp2+1]A[pp2] |
| UGK pixel | max2=PP2+(a−1)/(2a+2) Half width=sqrt(8ln2) (IPP2-Maxi-0,5)/ln(A(PP2+/−1)/A(PP2))) | max1=0,5-PP-half width* (ln(A[PP])/sqrt(8ln2)
IF max1 < 0 THEN
max1=0,5+PP+half width* (ln(A[PP−1]/A[PP]sqrt(8ln2)
A(max1)=A[PP]*exp(0,5*sqrt(PP-max1)/sqrt(half width/sqrt(8ln2)))
A(UG(=Untergrund[=background]))=A(max1)*exp(0.5*sqrt(Pix-max1) sqrt(half width/sqrt(8ln2)))
A(pix)=A(measured)−A(UG)

I claim:

1. A method for determining concentrations by means of atomic absorption spectroscopy using an atomic absorption spectrometer, said spectrometer including:

a continuous source as a source of radiation;

a high resolution monochrometer element; and a detector consisting of a plurality of detector elements, said method comprising:

measuring the radiation intensity of the source impinging on each detector element;

introducing a sample consisting of at least one known element to be quantified and at least one unknown component into said spectrometer;

determining an uncorrected absorbance at each detector element at a plurality of times, to form an uncorrected absorbance spectrum for each time;

determining a broadband background absorbance function from each of said uncorrected absorbance spectra;

subtracting each of said broadband background absorbance functions from each of said uncorrected absorbance spectra to yield a first corrected absorbance spectrum for each of said plurality of times;

comparing each first corrected absorbance spectrum at a particular detector element corresponding to the known sample element at each particular time with each first corrected absorbance spectrum at at least one adjacent detector element at each particular time;

determining if a relationship between the first corrected absorbance measured at the particular detector element corresponding to the known sample element and the first corrected absorbance measured at said at least one adjacent detector element fluctuates by more than a predetermined amount over time indicating an interfering background absorbance;

determining a profile of said interfering background absorbance;

determining a spectral position of said interfering background absorbance by determining where said fluctuation of said relationship between said first corrected absorbance measured at the particular detector element corresponding to the known sample element and said first corrected absorbance measured at said at least one adjacent detector element is a maximum;

calculating a magnitude of the interfering absorbance from said spectral position and said profile; and subtracting said magnitude from said first corrected absorbance.

2. The method of claim 1 where said broadband absorbance functions are determined by choosing correlation coefficients that correspond to the minima of said uncorrected absorbance spectra.

3. The method of claim 1 wherein said unknown component produces an atomic line.

4. The method of claim 3 wherein said interfering background absorbance is due to said atomic line.

5. The method of claim 4 wherein said profile is measured prior to sample measurement.

6. The method of claim 1 wherein said unknown component comprises a molecule.

7. The method of claim 6 wherein said interfering background absorbance is due to said molecule.

8. The method of claim 7 wherein said profile is determined by using an isolated molecule line in the measured spectral region.

9. The method of claim 1 wherein at least one of said broadband background absorbance functions is a polynomial.

* * * * *